United States Patent [19]

Plumridge

[11] 4,111,190

[45] Sep. 5, 1978

[54] MEDICAL APPLICATOR ASSEMBLY FOR CHAIN CYSTOURETHROGRAPHIC PROCEDURE

[76] Inventor: Jane Plumridge, 17 Stoney Brook Dr., Glastonbury, Conn. 06033

[21] Appl. No.: 741,151

[22] Filed: Nov. 11, 1976

[51] Int. Cl.² .............................................. A61B 6/00
[52] U.S. Cl. ............................. 128/2 A; 128/303 R; 128/349 R; 128/DIG. 9; 250/312
[58] Field of Search ................ 128/2 A, 2 M, 1.3–1.5, 128/130, 303 R, 348, 349 R, 350 R, 356, DIG. 9; 250/312

[56] References Cited

U.S. PATENT DOCUMENTS

| | | | |
|---|---|---|---|
| 3,200,815 | 8/1965 | Marguiles | 128/130 |
| 3,369,542 | 2/1968 | Thaidigsman | 128/2 A |
| 3,421,499 | 1/1969 | Bray et al. | 128/348 X |
| 3,492,990 | 2/1970 | Clarke | 128/130 |
| 3,794,041 | 2/1974 | Frei et al. | 128/2 M X |
| 3,820,535 | 6/1974 | Marco | 128/130 |
| 3,844,274 | 10/1974 | Nordstrom | 128/2 M |
| 3,941,119 | 3/1976 | Corretes | 128/2 M |

FOREIGN PATENT DOCUMENTS 32,130  8/1923  Denmark .................. 128/356

*Primary Examiner*—Lee S. Cohen
*Attorney, Agent, or Firm*—Prutzman, Hayes, Kalb & Chilton

[57] ABSTRACT

A medical applicator assembly for a chain cystourethrographic procedure requiring only a single catheterization comprises a flexible intra-medic plastic tubing having a hollow longitudinal passage with coaxial proximal and distal openings at opposite ends, a metallic bead chain loosely and slideably positioned within the passage and having a soft tip secured to the proximal end of the chain, the tip comprising a stem portion slideably received within the proximal end opening of the passage and an integral head portion of larger diameter than the passage and of blunt tapered configuration and a flexible rod-like plunger of substantially smaller diameter than the passage for slideably displacing the chain relative to the tubing so as to dislodge the stem portion from the proximal opening of the tubing.

7 Claims, 2 Drawing Figures

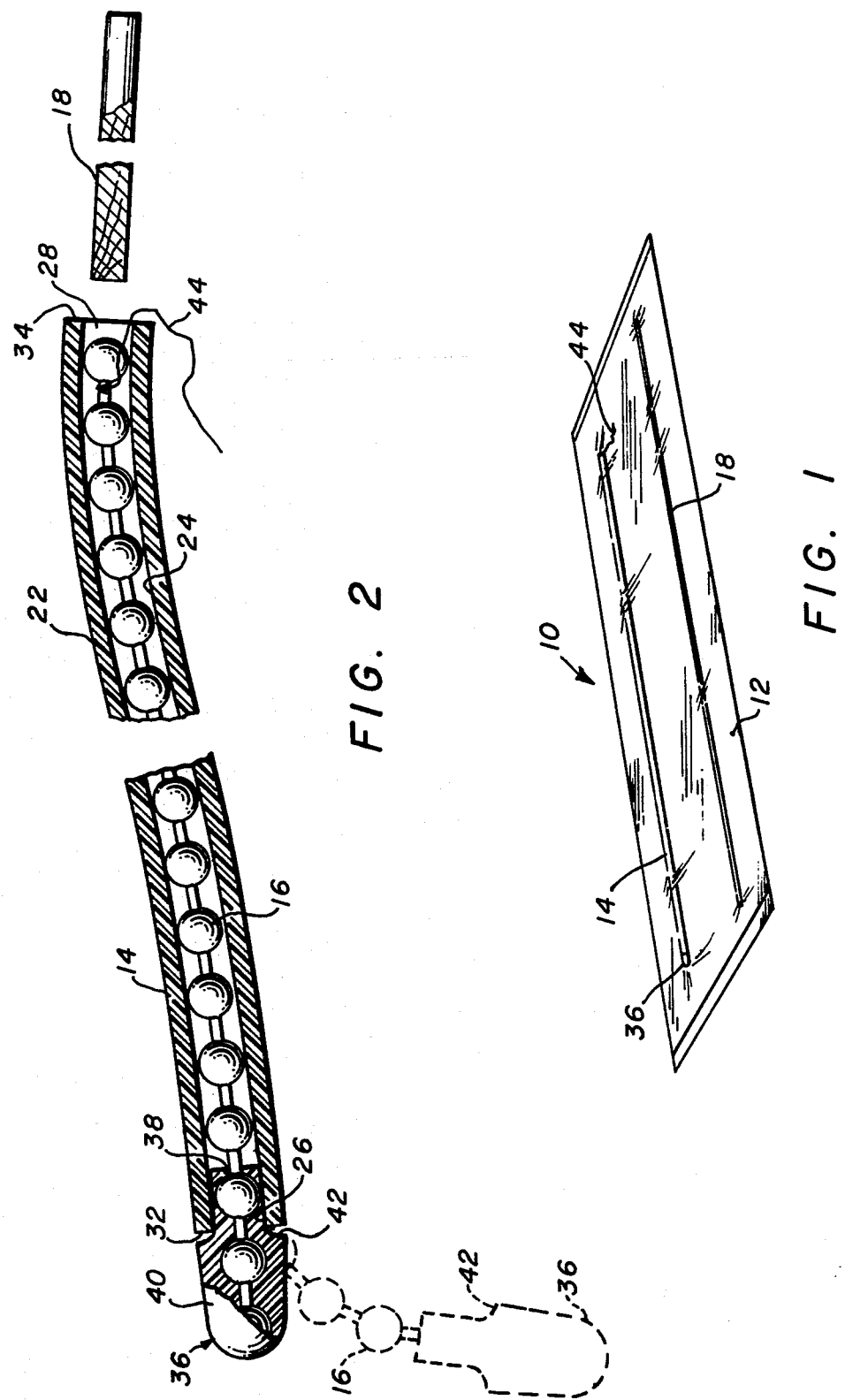

MEDICAL APPLICATOR ASSEMBLY FOR CHAIN CYSTOURETHROGRAPHIC PROCEDURE

BACKGROUND AND SUMMARY OF THE INVENTION

The present invention relates to a medical applicator assembly used as an aid in performing a radiological examination of a urinary bladder.

Many women experience occasional trivial degrees of urinary loss which needs no treatment. However, more frequent urinary incontinence during the stress of increased intra-abdominal pressure, such as occurs on sneezing or coughing, may be symptomatic of anatomic abnormalities that require treatment. Frequently, urinary incontinence is due to loss of the urethrovesical angle, that is, the angular relationship between the bladder and the urinary canal. Normally, the bladder slants obliquely downwardly and forwardly from the opening of the urinary canal forming an angular relationship therebetween which is approximately 90°. Injury to the muscles and other ligaments which support the floor of the bladder or other conditions can result in a displacement of that angular relationship and an inability to control urine flow.

As mentioned, this urine control problem is only symptomatic of a bladder displacement condition and it is necessary for the physician to determine the existence and extent of any displacement in order to evaluate the need for surgical correction. Accordingly, prior to the initiation of any corrective surgical procedure of this type, it generally has been the practice to perform a cystourethrographic examination. In this procedure, a radiopaque liquid contrast media or dye and a metallic bead chain are used to study the angular relationship of the urinary canal to the bladder. During this procedure, a bead chain and contrast media are deposited within the bladder with the chain extending into the urinary canal. The chain conforms to the floor of the bladder so that when the X-ray or roentgenogram is taken, the physician is able to readily observe its contour along the floor of the bladder and through the urethra thereby also observing and determining the relative angular position between these members. Normally, if the angle is greater than 120°, a surgical procedure will be performed to correct the displacement and re-establish or restore the usual urethrovesical angle. After such surgical procedures, it is also conventional to perform a post-operative cystourethrogram to ensure that proper angular orientation has been achieved.

In accordance with prior art techniques, the cystourethrographic procedure involved the insertion of a catheter into the bladder so that the bladder could be drained immediately prior to injection of the radiopaque contrast solution. The catheter was then removed and one of two alternative procedures were followed. In accordance with one procedure, the removed catheter was split longitudinally along its entire length. The chain was then inserted into the split catheter and the catheter was reinserted through the urethra into the bladder in order to deposit the chain therein. In accordance with this technique, the catheter and the chain were disengaged after insertion and the catheter was removed or withdrawn leaving the chain in place in the urethra and the bladder. Unfortunately at times, the chain was not fully disengaged from the catheter resulting in at least partial extraction of the chain as the catheter was removed, thereby necessitating a repetition of the catheterization procedure. In accordance with the alternative technique, the chain was inserted by flexible forceps which manipulated the chain through the urethra in a link-by-link manner until the chain had been properly positioned within the bladder. The forcep method was often painful to the patient and required a physician of exceptionally high skill. A variation of the forcep procedure is disclosed in Nordstrom's U.S. Pat. No. 3,844,274. As will be appreciated, in both procedures, it was necessary to initially catheterize the patient to introduce the contrast media, remove the catheter and conduct a subsequent catheterization or forcep manipulation in order to properly locate the bead chain within the bladder.

A single catheterization procedure is described in Thaidigsman's U.S. Pat. No. 3,369,542 where a metal catheter was fixed to a housing block used for injecting the contrast liquid. A trailing wire of twice the length of the chain was secured to the chain and preloaded into the metal catheter through a radial opening spaced from the tip of the catheter. The present invention also avoids multiple catheterization, as well as the discomfort associated with the prior procedures, yet advantageously utilizes a substantially more simplified, economical and disposable construction well suited to easy, trouble-free and effective use.

Another feature of the present invention is the provision for a new and improved medical applicator assembly for use in a chain cystourethro examination of the type described which provides for a quicker, easier and relatively painless means of accurately depositing a metallic bead chain and contrast media within the bladder of the patient thereby rendering the patient more comfortable and reducing the length of time of the procedure.

Still another object of the present invention is to provide a medical applicator assembly of the type described that can be inexpensively produced as a highly flexible, disposable, sterilized assembly or as a partially disposable assembly thereby permitting not only a one time catheterization but at the same time avoiding the chance of inadvertent infection from reuse. Included in this object is the provision for disposability within those portions of the assembly which can be manufactured and replaced inexpensively.

Other objects will be in part obvious and in part pointed out more in detail hereinafter.

These and related objects are achieved in accordance with the present invention by providing a medical applicator assembly comprising a flexible intramedic tubing having a smooth uninterrupted outer surface and a hollow longitudinal passage extending axially along the entire length thereof with coaxial proximal and distal openings at opposite ends of the passage. A metallic bead chain of substantially the same length as the tubing is loosely and slideably positioned within the passage and is provided with a soft tip secured to the proximal end of the chain by embedding at least one bead of the chain therein. The tip is comprised of a stem portion that is slideably received within the proximal end opening of the passage and an integral head portion of larger diameter than the passage and of blunt tapered configuration, the tip extending axially beyond the proximal end of the tubing. The head portion of the tip forms a shoulder with the stem portion, which shoulder abuts the proximal end of the tubing and maintains the tip in assembled relationship with the tubing during the insertion of the tubing through the urinary canal and into the bladder of the patient. A flexible rod-like plunger of substantially smaller diameter than the passage is used to engage the distal end of the chain and slideably displace the chain relative to the tubing so as to dislodge the stem portion from the proximal opening of the tubing. The distal opening of the tubing is connectable to a reservoir of radiopaque high contrast fluid which can then be inserted into the bladder through the tubing prior to fully dislodging the chain and removing the tubing.

A better understanding of this invention will be obtained from the following detailed description and the accompanying drawing of an illustrative application of the invention.

BRIEF DESCRIPTION OF THE DRAWING

In the drawing:

FIG. 1 is a perspective view of a sterilized package incorporating the medical applicator assembly of the present invention; and FIG. 2 is an enlarged fragmentary side view, partially broken away and partially in section, of the medical applicator assembly of FIG. 1.

DESCRIPTION OF THE PREFERRED EMBODIMENTS

Referring now to the drawing in greater detail wherein like reference numerals indicate like parts within both figures, there is shown in FIG. 1 a sterilized package 10 containing the medical applicator assembly of the present invention housed within a sealed wrapping 12 or the like which may be partially or fully transparent, as illustrated. The wrapping 12 may be of any suitable material capable of maintaining the contents of the package in the desired sterilized condition for prolonged periods of storage and prior to use. The assembly within the package 10 consists of an elongated plastic tubing 14 having a metallic bead chain 16 assembled therein and a flexible rod-like plunger 18 for use in dislodging and separating the chain from the enclosing tubing. Typically, the tubing 14 and metallic bead chain 16 are of substantially the same length, e.g., approximately 25 cm. in length, while the flexible rod-like plunger 18 is of somewhat greater length, namely, about 5 centimeters longer, in order to assure complete and full dislodgement between the plastic tubing 14 and the chain 16 carried therein.

As best shown in FIG. 2, the elongated intramedic tubing 14 is a flexible plastic member and is provided with a smooth uninterrupted outer surface 22 and an elongated longitudinally extending passage 24 which extends axially along the entire length of the tubing. The passage 24 terminates in coaxial proximal and distal openings 26 and 28 respectively at opposite ends of the passage 24. In the preferred embodiment illustrated, the opposite ends of the tubing 14 exhibit flat butt surfaces 32, 34 respectively that lie within a plane perpendicular to the axis of passage 24. However, the end surfaces can be disposed at a slight angle to the axis of the passage to facilitate attachment and release of the tubing during use. As will be appreciated, the tubing should be formed of inert plastic material well accepted in the medical industry for use as a catheter, such as Tygon tubing and the like.

The metallic bead chain 16 is of the type conventionally employed in cystourethro examination and is constructed of a material which can be readily sterilized and re-sterilized for subsequent use, if desired. In accordance with the present invention, the terminal beads of the bead chain 16 are firmly embedded and encased within a soft, pliant and medically acceptable plastic material such as a silicone plastic or the like, for example Silastic. The plastic embedding the terminal bead of the chain is molded into a tip 36 which has a stem portion 38 of slightly smaller diameter than the inside diameter of the passage 24 and an enlarged head portion 40 that is slightly rounded and tapered on its free end and exhibits a diameter substantially equal to the exterior diameter of the tubing 14. A rear shoulder 42 on the head portion 40 at its area of interconnection with the stem portion 38 abuts the proximal end surface 32 of the tubing 14 when the stem is positioned within the passage 24. As shown, the opposite or distal end of the chain 16 may have a short length of thread-like material 44, such as nylon suturing material, secured to the chain and extending outwardly of the tubing opening 28 so that by simply pulling on the suturing material the physician is able to maintain a firm interconnection between the tip 36 and the proximal end surface 32 of the tubing. In this manner, the tip is maintained in coaxial alignment with the tubing such that the tip and tubing act as a single unit upon insertion through the urinary canal of the patient. If desired, a slit (not shown) can be provided in the distal tube surface 34 to receive and secure the retaining thread 44 while the chain and tube assembly is in use.

In operation, the assembled metallic bead chain 16 and tubing 14 are inserted into the bladder through the urethra for a sufficient distance to place the tip 36 well within the bladder cavity. The flexible rod-like plunger 18, which is of plastic or wood, as illustrated, and of substantially smaller diameter than the passage, is then inserted into the passage 24 through distal end opening 28 of the tubing while holding the tubing 14 in place. The plunger abuts the distal end of the chain and drives the chain relative to the tubing to dislodge the stem portion 38 of the tip from the tubing. Since the chain is loosely and slideably positioned within the passage, the release of the tip permits the tip to fall toward the floor of the bladder in the manner shown in phantom in FIG. 2. The plunger 18 then is removed from the distal end opening 28 of the tubing, freeing that end for connection to a source of radiopaque high contrast liquid which can be fed through the passage into the bladder either by a gravity feed or by the use of a syringe or the like. If desired, the distal end of the tubing may be flared to facilitate the interconnection of the tubing with the source of the contrast liquid. Upon completion of the injection or flow of the contrast media, the tubing 14 is disconnected from the liquid supply and the plunger 18 is reinserted into the tubing until it re-engages the chain. Thereupon, the bead chain 16 is further displaced to assure its proper positioning on the floor of the bladder with a portion of the chain remaining within the tubing located in the urethra. The chain is maintained in its proper position by the plunger as the tubing is withdrawn to effect full disengagement between the tubing 14 and the chain 16. At this point, the exact positioning of the chain can be modified or corrected as needed and the exposed end thereof can be secured to the patient by means of adhesive tape or the like or the tape may simply be applied to the thread-like suture material 44 connected to the distal end of the chain. The patient is then ready for the series of X-rays following which the chain can be readily removed.

As will be apparent to persons skilled in the art, various modifications, adaptations and variations of the foregoing specific disclosure can be made without departing from the teachings of this invention.

I claim:

1. In a medical applicator assembly for use in a cystourethro examination comprising a tubing having a hollow longitudinal passage, a metallic bead chain loosely and slideably positioned within said passage and means for slideably displacing said chain from said passage, the combination wherein said tubing is a flexible elongated plastic tube having a smooth uninterrupted outer surface and a passage extending axially along the entire length thereof with coaxial proximal and distal openings at opposite ends of said passage, said chain being of substantially the same length as the tubing and having proximal and distal ends with a soft sterile tip secured to the proximal end of said chain, said tip comprising a stem portion snugly received within said passage, an integral head portion larger than said passage and an intermediate shoulder connecting said stem and head portions and abutting the end of said tubing at said proximal opening, said chain being firmly embedded in said tip, said head portion extending beyond the proximal end of said tubing axially of said passage and having a tapered surface with a maximum diameter substantially equal to the diameter of the outer surface of said tubing, said shoulder extending radially from said stem portion to said tapered surface, said chain including means for holding said tip in alignment with said tubing and said shoulder in engagement with said tubing to facilitate insertion of said tip and the proximal end of said tubing through the urinary canal and into the bladder of a patient, said displacing means being an independent member movable into engagement with the distal end of said chain for slideably displacing the chain relative to the tubing and dislodging said stem portion from said passage.

2. The assembly of claim 1 wherein said stem portion provides at least a part of said means for holding said shoulder in engagement with the tubing.

3. The assembly of claim 1 wherein said tip firmly embeds at least one bead of said chain.

4. The assembly of claim 1 wherein said displacing means includes an independent flexible rod-like plunger movable into and out of engagement with the distal end of said chain.

5. The assembly of claim 4 wherein the plunger is of substantially smaller diameter and longer length than said passage for dislodging said tip from the proximal end of said tubing upon insertion within said passage.

6. The assembly of claim 1 wherein chain holding means includes a thread-like member secured to the distal end of said chain.

7. The assembly of claim 6 wherein said thread-like member extends outwardly of said tubing for drawing said shoulder into firm engagement with said tubing and maintaining said engagement during said insertion.

* * * * *